(12) United States Patent
Tsukita

(10) Patent No.: US 6,559,286 B1
(45) Date of Patent: May 6, 2003

(54) ANTIBODIES TO OCCLUDIN PROTEINS

(75) Inventor: Shoichiro Tsukita, Kyoto (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/197,503

(22) Filed: Nov. 23, 1998

Related U.S. Application Data

(62) Division of application No. 08/945,826, filed as application No. PCT/JP97/00665 on Mar. 5, 1997.

(30) Foreign Application Priority Data

| Mar. 7, 1996 | (JP) | ................................................ 8-49880 |
| Dec. 12, 1996 | (JP) | ............................................. 8-331944 |

(51) Int. Cl.⁷ ............................................. C07K 16/28
(52) U.S. Cl. .............................. 530/387.9; 530/387.1; 530/388.1; 530/388.2; 530/389.1; 530/391.1; 530/391.3
(58) Field of Search ........................ 435/7.1; 530/387.1, 530/388.2, 389.1

(56) References Cited

FOREIGN PATENT DOCUMENTS

| JP | 60 500684 | 5/1985 |
| WO | WO 84 03564 | 9/1984 |

OTHER PUBLICATIONS

Hirase et al. Kekkan to Naihi 4(4): 349–357 (1994).*
Hirase et al. Kekkan to Naihi 4(4): 349–357 (1994) English Translation.*
Akatsuka Cell Structure and Function 20: 585, (1995).*
Furose et al. J Cell Biol 127: 1617–1626, (1994).*
GenBank Accession Nos. U49184, U49185, U49221 Submitted Feb. 1, 1996; Ando–Akatsuka, Kyoto University Faculty of Medicine, Japan.*

M. Takeichi, *Science,* vol. 251, pp. 1451–1455 (1991).
R.S. Buxton, et al., *Journal of Cell Biology,* vol. 121, No. 3, pp. 481–483, (May 1993).
E.E. Schneeberger et al., *Am. J. Physiol.,* vol. 262, pp. L647–L661 (1992).
S. Tsukita et al., *Current Opinion in Cell Biology,* vol. 4, pp. 834–839 (1992).
M. Furuse et al., *The Journal of Cell Biology,* vol. 123, No. 6, Part 2, pp. 1777–1788 (Dec. 1993).
N. Roy et al., *Cell,* vol. 80, pp. 167–178, (Jan. 1995).
P. Chomczynski et al., *Analytical Biochem.,* vol. 162, pp. 156–159 (1987).
P.D. Cook, *Anti–Cancer Drug Design,* vol. 6, pp. 585–607 (1991).
Y. Ando–Akatsuka et al, *The Journal of Cell Biology,* vol. 133, No. 1, pp. 43–47 (1996).
A.M. Maxam et al., *Proc. Natl. Acad. Sci. USA,* vol. 74, No. 2, pp. 560–564 (Feb. 1977).
F. Sanger et al., *Proc. Natl. Acad. Sci. USA,* vol. 74, No. 12, pp. 5463–5467, (Dec. 1977).
C. Gorman et al., *Science,* vol. 221, pp. 551–553 (1983).
G. Kohler, et al., *Nature,* vol. 256, pp. 495–497.
U. Gubler et al, *Gene,* vol. 25, pp. 263–269 (1983).

* cited by examiner

*Primary Examiner*—Phillip Gambel
(74) *Attorney, Agent, or Firm*—Birch Stewart Kolasch & Birch LLP

(57) ABSTRACT

The present invention discloses antibodies that bind to mammalian occludin proteins which are transmembrane adhesion molecules of the tight junction. Nucleic acid and amino acid sequences encoding human, mammalian, and murine occludin are utilized to prepare and isolate occludin-specific antibodies. These antibodies may be used to elucidate and regulate the activities of tight junctions.

9 Claims, 1 Drawing Sheet

ANTIBODIES TO OCCLUDIN PROTEINS

Application Ser. No. 08/945,826 is the national phase of PCT International Application No. PCT/JP97/00665 filed on Mar. 5, 1997 under 35 U.S.C. §371. The entire contents of each of the above identified applications are hereby incorporated by reference.

This application is a divisional application of U.S. application Ser. No. 08/945,826 filed Nov. 5, 1997.

The present invention relates to an amino acid sequence of membrane protein occludin in a tight junction (hereinafter referred to as "the TJ") of a human, a dog and a mouse, and a DNA for encoding the amino acid sequence. Antibodies that bind to the occludin protein or portions thereof are also included in the present invention.

BACKGROUND OF THE INVENTION

In multicellular animals, the information on cellular adhesion between adjacent cells is deeply concerned with the regulation and maintenance of vital phenomena such as cellular proliferation and differentiation, inflammation and cancer metastasis. Intercellular adhesion molecules which take part in the adhesion of the cells frequently assemble together on the surfaces of these cells to form a specifically differentiated membrane region for the adhesion. Particularly, intercellular adhesion molecules such as cadherins are known to be firmly bound to cytoskeleton in the cytoplasmic domain of epithelial cells. Such membrane regions are called intercellular adhesion apparatus and chiefly classified into the following four structures: gap junction (GJ), adherens junction (AJ), desmosome and tight junction (TJ).

These adhesion apparatus has first been identified under an electron microscope, and as a result of the investigation and research of constituent proteins, the importance of their physiological and pathological significance has become the focus of increased interest. The proteins that are called the so-called adhesion molecules specifically exist in these adhesion apparatus, and the adhesion molecules of the AJ are cadherins and various kinds of cadherins such as N-cadherin and P-cadherin have been identified so far [Takeichi, M. et al., "Science", Vol. 251, p. 1451–1455, (1991)]. As adhesion molecules of the desmosome, desmoglein and desmocollin are known, and according to recent studies, it has been elucidated that their structures are similar to those of the cadherins [Buxton, R. S. et al., "J. Cell Biol.", Vol. 121, p. 481–484, (1993)]. The adhesion molecules of the GJ are called connexin, and it is known that connexin holds transmembrane domains at four different sites and both of its N-terminal and C-terminal protrude on the cytoplasmic side of the membrane.

The TJ is an intercellular adhesion apparatus peculiar to epithelial cells and endothelial cells, where the cell membranes of contiguous cells are seen completely tightly apposed. The TJ surrounds individual cells and functions as a barrier to block or regulate permeation of water-soluble molecules between the luminal and basement membrane sides of a cell layer. It has also been described to act as a fence partitioning the cell membrane into apical and basolateral sides in order to maintain the polar distribution of such membrane proteins as ion channels and pumps as well as lipids on the cell membrane [Schneeberger, E. E. et al., "Am. J. Physiol.", Vol. 262, P. L647–L661, (1992)]. Owing to these functions of the TJ, milieus consisting of different fluid compositions are formed on the opposite sides of a cell layer, so that the polarity of the cell layer is maintained; hence the TJ can be said to be a fundamental structure of vital importance to multicellular organisms.

However, analysis of the molecular structure of the TJ has been less progressing, compared to other adhesion apparatus. In fact, it has constituted a serious drawback to the pursuit of molecular biological research on the TJ that the TJ adhesion molecule itself has not been identified yet.

The present inventors have established a method for isolation of AJ from rat liver, and have identified many proteins such as radixin and ZO-1 from this isolated AJ [Tsukita, Sh. et al., "Curr. Opin. Cell Biol.", Vol. 4, P. 834–839, (1992)]. From researches on ZO-1 and histologic findings for the AJ and the TJ, it can be presumed that the proteins in the AJ also contain protein of the TJ. In view of this, the present inventors have isolated AJ from chick liver, prepared a monoclonal antibody against the AJ as the antigen, and carried out structural analysis of the TJ-constituting protein using the antibody specifically reacting with the TJ. As a result, the present inventor has been successful in the structural analysis of a novel constituent protein dissimilar to known proteins, and designated the protein as occludin [Furuse, M. et al., "J. Cell Biol.", Vol. 123, p. 1777–1788, (1993)].

This chick occludin is a 56 KDa protein composed of 504 amino acids, characterized conspicuously by transmembrane domains at four sites in the half of its N-terminus, with both the N- and C-terminals facing the cytoplasm and with two extracelluar loops.

From subsequent studies, occludin was inferred to be an important factor in the analysis of physiological function of the TJ at the cellular level as well as at the whole body level, and drew much attention of investigators.

No further study has progressed, nevertheless, since the said protein has its origin in the chicken species greatly remote from humans. Thus, structural analysis of occludin of human origin has been expected for the sake of elucidation of the physiological function and medical analysis of the TJ. There is as yet no report of success in the elucidation of human occludin despite worldwide competition in research for this purpose in this field.

SUMMARY OF THE INVENTION

It is accordingly an object of the present invention to provide amino acid sequences of human, canine and mouse occludins and the DNAs encoding them.

In their report on the gene for human neuronal apoptosis inhibitory protein (NAIP), Roy et al. documented occurrence of a DNA fragment possessing a base sequence analogous to the C-terminal region of chick occludin in NAIP gene deletion mutants [Roy, N. et al., "Cell", Vol. 80, p. 167–178, (1995)]. To ascertain whether the said sequence actually encoded a part of human analogue of occludin or not, the present inventor selected primers out of the base sequence analogous to that of chick occludin and made a scrupulous screening with a cDNA library of human intestinal epithelial cell strain T84 as a template for PCR. The present inventor has thus succeeded in the analysis of the whole structure of human occludin. Further, the inventor has completed analyses of mouse and canine occludins, prepared anti-occludin monoclonal antibodies, and verified with histologic staining that the occludins were transmembrane type TJ proteins.

BRIEF DESCRIPTION OF THE DRAWINGS

FIG. 1A is a stained immunofluorescent photomicrograph of cultured human intestinal epithelial cell strain T84 with an anti-human occludin rat monoclonal antibody.

FIG. 1B is a stained immunofluorescent photomicrograph of cultured human intestinal epithelial cell strain T84 with a mouse monoclonal antibody against the TJ lining protein ZO-1. The same sites of T84 were photographed.

Figure 1:
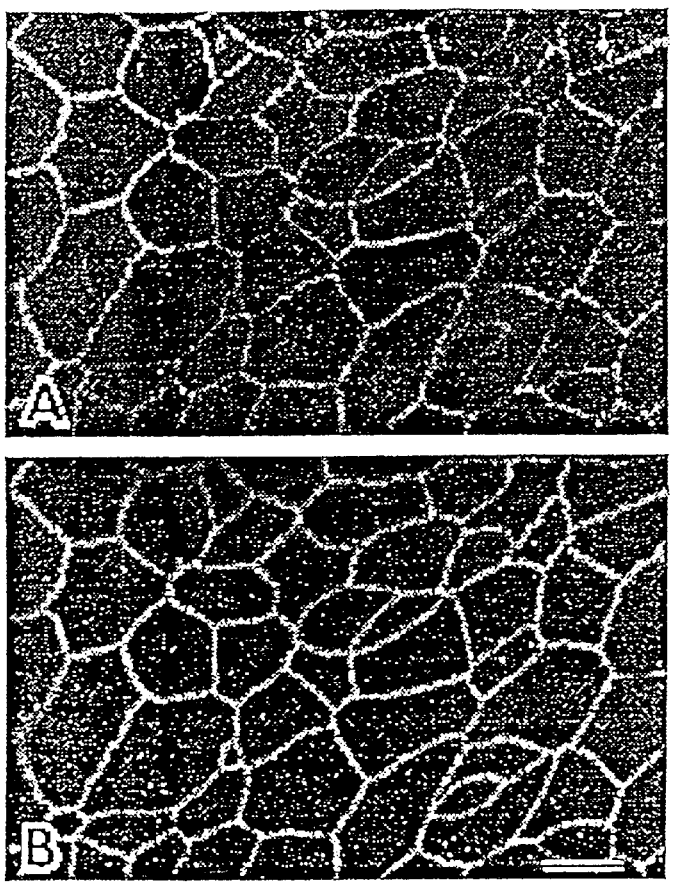
FIGS. 1A–B are photographs substituting for drawings showing the morphology of organisms.

The present invention is concerned with amino acid sequences of a human, a canine and a mouse occludin, DNAs for encoding them, anti-occludin antibodies, and a genetic analysis method utilizing them. More specifically, the present invention is directed to the following aspects.

(1) A DNA for encoding a human occludin having an amino acid sequence described in Sequence No. 2.
(2) A DNA for encoding a human occludin as described in Sequence No. 7.
(3) A DNA described in Sequence No. 3 for encoding a canine occludin having an amino acid sequence described in Sequence No. 4.
(4) A DNA described in Sequence No. 5 for encoding a mouse occludin having an amino acid sequence described in Sequence No. 6.
(5) A human, a canine and a mouse occludin having the amino acid sequences described in Sequence Nos. 2, 4 and 6, respectively.
(6) An occludin variant having an amino acid sequence in which one or plural amino acids in the amino acid sequence of each occludin are added, deleted or substituted, and a DNA for encoding the variant.
(7) A vector which comprises any of DNAs for encoding a human, a canine or a mouse occludin or for encoding their variants.
(8) A transformant which holds the vector.
(9) A method for manufacturing an occludin protein which comprises the steps of cultivating the transformant, and collecting an expressed product.
(10) A DNA probe comprising containing the whole or part of the base sequence as defined in Sequence No. 1, 3 or 5.
(11) A DNA primer comprising containing part of the base sequence as defined in Sequence No. 1, 3 or 5.
(12) A polyclonal antibody or a monoclonal antibody specifically binding to a human, a canine or a mouse occludin protein.
(13) An assay method and an assay reagent for occludin in a biological specimen, wherein an anti-occludin antibody is used.
(14) An analysis method of an occludin gene in a biological specimen, wherein said DNA primer or said DNA probe is used.
(15) A screening method of a drug affecting the expression of occludin, wherein occludin-expressing cells and an analyte are allowed to coexist, and an expression quantity of an occludin gene of said cells is then determined by the use of a DNA primer or a DNA probe.
(16) An antisense DNA derived from a human occludin DNA.
(17) A laboratory animal whose occludin DNA is knocked out.

BRIEF DESCRIPTION OF DRAWINGS

FIG. 1: Photographs of Immunofluorescence staining of cultured human intestinal epithelial T84 cells.

(a) immunofluorescence from rat anti-human occludin monoclonal antibody staining of cultured human intestinal epithelial cells (T84).

FIG. 1B; immunofluorescence of the same site from mouse monoclonal antibody against the TJ-lining protein ZO-1.

DETAILED DESCRIPTION OF THE INVENTION

With the success of the present inventor in identifying occludin analogues of mammals, it is now possible to structurally and functionally test the constitution and function of the TJ at the molecular level. The barrier and fencing functions of the TJ and the related regulatory mechanisms can be analyzed through experiments involving control of expression of the gene for occludin or inhibition of the occludin function with either an antisense probe or an antibody, using various types of cultured human, mouse and canine (MDCK) cells. For example, it is now possible to determine whether or not overexpression of occludin cDNA gives rise to an increase in number of TJ strands seen in freeze-fractured replicas and incidentally to an augmentation of the barrier function. Furthermore, the present invention has made it possible to establish a simple screening method for drugs affecting TJ function. For example, drugs affecting TJ function can be screened using various types of cells expressing occludin, by allowing the cell to react with a test article and subsequently by measuring the amount of cellular occludin gene or occludin protein expression. The gene analysis can be carried out by using a DNA probe or primer or other devices. It may be conducted by known methods, e.g. the Northern blot technique or Southern blot technique wherein RNA or DNA extracted from a test sample in the usual manner is pretreated when necessary, then electrophoresed on a membrane or gel, and hybridized with a labeled DNA probe, and the polymerase chain reaction (PCR) technique wherein the objective DNA is amplified using primers of about 20 bases corresponding to the relevant site and with a genomic DNA or cDNA as the template. The occludin protein can be quantitated, for example, by the use of an antibody.

Moreover, it is also made possible to ascertain how the TJ formation is involved in the morphogenesis of various organs and whether functional failure of the TJ has any relation to various pathologic states such as inflammation and tumor metastasis, by preparing various types of mutant mice and occludin gene-knocked out mice. The possibility of controlling a TJ function, especially its barrier function, is also of interest in connection with drug permeability. Thus, it would be feasible to control the blood-brain barrier via up- or down-regulation of occludin synthesis in epithelial cells of the brain. Control of the TJ function in the enteric epithelial cells is necessary to regulate drug absorption from the intestine. It will thus become possible to control drug absorption, particularly distribution to the brain tissue, by administering an effective substance screened out of drugs affecting the TJ function. Hence, the present invention is highly anticipated for elucidation of the physiological mechanisms primarily of the blood-brain barrier, as well as for analysis, diagnosis and treatment of disease states.

The DNA provided by the present invention can be utilized in the analysis of genes for occludin proteins and of gene expression thereof by using a part of it as a primer or a probe. The term a part here denotes that the oligonucleotide to be used as a primer or probe comprises containing at least a 10-relevant-base sequence, or preferably at least a 15-base sequence, or more preferably a corresponding polynucleotide comprising containing approximately 20- to 30-base sequence based on the DNA sequence of the present invention. As the probe, a higher macromolecular or even the whole DNA may be used.

There is a method utilizing antisense DNA or antisense RNA as a means to control the function of occludin. The method is intended to block the flow of gene expression by interfering with the reading of genetic information at any of the stages of gene expression such as DNA replication, transcription and translation, and the antisense technique employs nucleic acid or its analogue for the blockage (Wickstrome, E. ed., Prospects for Antisense Nucleic Acid Therapy of Cancer and AIDS. Wiley-Liss, New York, 1991). The elucidation of the occludin DNA according to the present invention has made possible the means for inhibiting occludin functions by the antisense method. The length of DNA oligomer has bearing on the double strand-forming capacity, membrane permeability and base sequence specificity; and at least 6 nucleotides, or preferably at least 10 mers, usually 15 to 30 mers, may be used. Appropriate sequences may be selected on the basis of the DNA sequence of the present invention, and verified by experimentation. Usually, the oligomer is chemically modified at its phosphate group, sugar moiety, and 3' and 5' tails in order to augment its stability (Cook, P. D., Anticancer Drig. Des., 5,585, 1991). Representative analogues are oligophosphorothioate where one of the oxygen atoms of the internucleoside phosphodiester group is replaced by a sulfur atom, and oligomethylsulfonate where the said oxygen is replaced by a methyl group; all such analogues are remarkably stable to nucleases. Besides, such oligomers as those with acridine or polylysine bonded to them and those containing N-methlythymidylate, to increase stability of the hybrid double strand, are also used. These oligomers can be synthesized by known chemical synthetic procedures. Antisense RNA derived from the DNA of the present invention may also be utilized.

The occludin protein of the present invention may be utilized for preparation of an antibody using the whole or a part of it as an epitope, and for use the antibody thus prepared as research and diagnostic reagents. The term epitope denotes an antigen determinant of polypeptide; epitope is usually comprised of at least 6 amino acids, and it is known that a polypeptide consisting of 6 amino acids combines with an antibody (JP-A-60-500684). The antigenic peptide of the subject protein signifies a polypeptide comprising a series of at least 6 amino acids, preferably a series of at least 8 amino acids, more preferably a series of at least 15 amino acids, or further preferably a series of at least 20 amino acids, based on the amino acid sequence of the present invention. Occludin provided by the present invention is a protein which, as inferred from its amino acid sequence in analogy with chick occludin, possesses transmembrane domains at four sites in a half of its N-terminal region, with the N- and C-terminus facing the cytoplasm, and which has two extracellular loops. In the case of human occludin of which amino acid 89–135 and 196–243 regions are presumed to be extracellularly apposed, various antibodies may be prepared by selecting antigenic sites appropriate for purposes and utilized as a means to elucidate the TJ function and as a means to suppression by the antibody of the TJ function. It is also possible to utilize the partial peptides as a means to screen compounds for those capable of binding to these peptides.

Proteins having an amino acid sequence of occludin of the present invention to which one or a plurality of amino acids are added or of which one or a plurality of amino acids are deleted or substituted are also encompassed by the present invention.

(1) Preparation of cDNA Library and Structural Analysis of Occludin

Preparation of RNA may be carried out using human or animal cells (cell strains) as the raw material, by for example extraction with a mixed solution of guanidine thiocyanate, a surfactant, a chelating agent and a reductant, followed by phenol extraction, fractionation in organic solvents (Chamezynski et al., Anal. Biochem., 162, 156, 1987) and subsequently density gradient ultracentrifugation procedure. Using the RNA thus obtained as a template, a double strand DNA is prepared in the usual manner such as by the cDNA synthesis technique (Gubler, U. et al., Gene, 25, 263, 1983) with the use of random primers, reverse transcriptase, DNA polymerase, etc. A DNA library can be prepared by insertion of the double strand DNA obtained into a bacteriophage such as λ zap or λ gt11 in the usual manner. Commercial cDNA libraries may also be used.

According to the report of Roy et al., it is possible to obtain a DNA fragment presumed to be of occludin DNA origin by properly selecting a primer region based on the base sequence analogous to the C-terminus of chick occludin, by amplification of the DNA with the PCR technique, and by its subclonation. Subsequent screening of the cDNA library with this DNA fragment as a probe and analysis of the base sequence of the clone isolated may yield a whole-length cDNA for occludin. The structure of the base sequence is determined by the Maxam-Gilbert method (Maxam, A. M. and Gilbert, W., Proc. Natl. Acad. Sci. USA, 74, 560, 1977) or by the dideoxynucleotide chain termination method (Sanger, F., Proc. Natl. Acad. Sci. USA, 74, 5463, 1977). The amino acid sequence is thus deduced on the basis of the base sequence. These gene manipulations can be performed by the known usual methods, for example in accordance with those described in Molecular Cloning. A Laboratory Manual, T. Maniatis et al. eds. (1989), Cold Spring Harbor Laboratory.

(2) Preparation of Antibodies

To prepare the monoclonal antibody according to the present invention, human, canine or mouse occludin is used as the antigen, its complex with a carrier protein is prepared if deemed necessary, and appropriate animals are immunized by inoculation with the antigen. Antibody-forming cells obtained from the spleen or lymphnodes of the above immunized animals are fused with myeloma cells, whereby hybridomas producing an antibody strongly specific to occludin are selected to prepare the monoclonal antibody. The preparation procedure may be in accordance with the known prior method.

As the immunogen, any of such products as purified natural products and products prepared by genetic recombination technique or chemical synthesis may be used. For preparation of occludin by the recombinant DNA technique, the cDNA encoding occludin can be religated to the promoter downstream of a vector appropriate for expression of occludin by the known method using restriction enzymes and DNA ligase to obtain a recombinant expression vector. The said vector is nonlimitative insofar as it can be replicated and amplified in a host. With regard to the promoter and terminator, there is also no particular limitation as long as they are concordant with the host used for expression of the base sequence encoding occludin; and appropriate combinations suited to the host may also be practicable. The recombinant expression vector thus obtained is introduced into the host by the competent cell technique (J. Mol. Biol., 53, 154, 1970) or the calcium phosphate procedure (Science, 221, 551, 1983) to prepare a transformant. Such organisms as *Escherichia coli* and animals are used as the host, and the transformant obtained is cultured in an appropriate medium suited to the host. The culture incubation is carried out usually at a temperature between 20° C. and 45° C. and at pH between 5 and 8, with aeration and/or stirring where required. Isolation and purification of occludin from the cultured microorganisms or cells may be performed by an appropriate combination of known methods of isolation and purification. These known methods include salting out, organic solvent method, dialysis, gel filtration, electrophoresis, ion exchange chromatography, affinity chromatography, and reverse-phase high performance liquid chromatography.

The immunogen, occludin, is preferably to retain its whole structure but may be in the form of a fragment or peptide having its partial structure; it may be appropriately selected from the whole amino acid sequence of occludin. For preparation of the fragment or peptide, a method such as chemical synthesis, the above mentioned gene recombination procedure or degradation of a naturally occurring article is employed.

Various condensing agents may be used for preparation of the immunogen-carrier protein complex; such reagents as glutaraldehyde, carbodiimide, and maleimide activated ester may be used.

The carrier protein may be any of those commonly used such as bovine serum albumin, thyroglobulin and hemocyanin, and usually the method wherein a 1- to 5-fold quantity of a carrier protein is coupled to antigen is used.

Animals employed for immunization include the mouse, rat, rabbit, and guinea pigs, and inoculation is made by subcutaneous, intramuscular or intraperitoneal injection. The administration of immunogen may be carried out in the form of a mixture with complete Freund adjuvant or with incomplete adjuvant, and is usually made once every 2 to 5 weeks. Antibody-producing cells obtained from the spleen or lymphnodes of the immunized animals are fused with myeloma cells and isolated as hybrydomas. The myeloma cells used are those of mouse, rat or human origin, preferably allogeneic to the antigen-producing cells used but, in some instances, can be xenogeneic.

The manipulation of cell fusion can be conducted in accordance, for example, with the method of Milstein and Köhler (Nature, 256, 495, 1975). Fusogens used include such agents as polyethylene glycol and Sendai virus, and the cell fusion can be made by incubating antibody-producing cells with myeloma cells in an approximate population ratio of 1:1 to 10:1 at a temperature between 20 and 40° C., preferably between 30 and 37° C., for about 1 to 10 minutes, using polyethylene glycol (mean molecular weight: 1,000 to 4,000) usually at a concentration of about 20 to 50%.

Various immunochemical methods can be used for screening hybridomas producing an anti-occludin antibody. The methods include enzyme-linked immunosorbent assay (ELISA) using microplates coated with occludin, enzyme immunoassay (EIA) using micoplates coated with an anti-immunoglobulin antibody, and Western blotting technique in which samples containing occludin are electrophoresed with the subsequent use of nitrocellulose transfer membranes.

Clones are obtained from these wells further by, for example, limiting dilution. Screening and breeding of hybridomas are performed in a culture medium for animal cells (e.g. RPMI 1640) containing 10–20% fetal bovine serum usually with added HAT (hypoxanthine, aminopterin and thymidine). The clone thus obtained is intraperitoneally transplanted into BALB/c mice previously dosed with bristan, and ascites containing a high concentration of a monoclonal antibody is collected 10–14 days later so that the ascites can be used as a source for purification of the antibody. Furthermore, the cloned hybridoma cells are cultured so that the cultured cells can be used as the source for purification of the antibody. Known methods for purification of immunoglobulin may be used for recovering the monoclonal antibody; the recovery can be readily accomplished for example by such means as ammonium sulfate fractionation, PEG fractionation, ethanol fractionation, utilization of anion exchangers, and affinity chromatography.

With immunological methods using the anti-occludin monoclonal antibody obtained in accordance with the present invention, it is possible to make qualitative and quantitative determination of occludin in biological specimens. As the immunological methods, conventional methods such as immunohistologic staining, enzyme immunoassay, agglutination test, competitive assay, and sandwich technique may be applied to samples from biological specimens that have been appropriately processed, where required, e.g. isolation of cells and extraction. The immunohistologic staining can be performed for example by the direct method using a labeled antibody or the indirect method using a labeled antibody directed to the antibody bound to target antigen. Any of such known labeling substances as fluorescent agents, radioactive substances, enzymes, metals and dyes may be used as labeling agents.

The monoclonal antibody of the present invention may be used in the form of Fab' or Fab fragment after removal of its Fc' or Fc region, or in the form of polymer of either fragment. Furthermore, it may also be in the form of a chimeric antibody, a humanized antibody, or a human antibody.

EXAMPLE

The present invention will now be illustrated in detail with specific embodiments by the following examples. Of course, the present invention shall not be limited to the following examples.

Example 1

Structural Analysis of Human Occludin

Based on a base sequence of a part of human NAIP-deficient gene analogous to the C-terminus of chick occludin, PCR was performed using as primers the oligonucleotides of Sequence Nos. 7 and 8. λgt11 cDNA library was prepared by purifying poly(A)+RNA from a source consisting of human intestinal epithelial cell strain T84 and by using TimeSaver cDNA Synthesis Kit (trade name; Pharmacia LKB Biotechnology Inc.)and GIGAPACK II Packaging Extract (Stratagene Inc.). The PCR was carried out with this library as the template and with said two primers yielded a cDNA fragment of 363 base pairs.

This DNA fragment was DIG-labeled using DIG Labeling Kit (trade name; Boehringer Mannheim), and said library was screened with it used as the probe. As a result, three cDNA clones were isolated, their insertion sites were cut, and they were subcloned to pBluescript SK(−). Of these, the two clones phOc6 and phOc16 were presumed to contain a total ORF, and these two cloned strands were analyzed for their base sequences, with the results demonstrating that said base sequences encoded the whole structure of human occludin. The coding sequence was determined using a 7-deaza Sequenase Version Deoxy Terminator Cycle Sequencing Kit (trade name; Applied Biosystems). The base sequence is shown in Sequence No. 1, and the amino acid sequence deduced therefrom in Sequence No. 2.

Structure of canine and mouse occludins were determined in the same manner as described above using λgt11 and λgt10 cDNA libraries, respectively, prepared from dog kidney (MDCK) cells and mouse lung cells. The base sequence and amino acid sequence of canine occludin are shown in Sequence Nos. 3 and 4, and the base sequence and amino acid sequence of mouse occludin in Sequence Nos. 5 and 6. *Escherichia coli* JM 109 containing the human occludin cDNA has been deposited (Deposition No. FERM BP-5477) with the National Institute of Bioscience and Human Technology, Ministry of International Trade and Industry, Japan (address: 1-1-3, Higashi, Tsukuba, Ibaraki, 305 Japan) as of Mar. 15, 1996.

Example 2

Preparation of an Anti-human Occludin Monoclonal Antibody

The cDNA fragment encoding the cytoplasmic region on the C-terminal side of human occludin was obtained by cutting the pBluescript SK(−) vector containing Sequence No. 1 described in Example 1 with restriction enzymes Ssp I and EcoR I (both being products of Takara Shuzo Co., Ltd.). This fragment was introduced into pGEX-3X vector, and *Escherichia coli* transformed with this vector was cultured to prepare a GST fused protein. Rats were immunized with this fused protein as an antigen, so that a monoclonal antibody was prepared.

The rat immunization was performed by injecting the antigen in doses of 300 µg/injection into the hindlimb paw, first as an emulsion with complete Freund adjuvant and the antigen alone twice thereafter (days 3 and 7 after the first). On the day following the last injection, inguinal lymphnodes were excised from the immunized animals and used for cellular fusion.

The rat lymphocytes and mouse myeloma P3 cells were combined in a ratio of 2.5:1, and the mixture was incubated in RPMI medium containing 1 g of polyethylene glycol (mean MW 4,000) dissolved in it, for 2 minutes according to a modified method of Köhler et al., to permit fusion of the cells. Fused cells were seeded in 24-well plates with HAT medium containing 10% HCF (Bokusui-Braun) for 9 days, followed by incubation in HT medium and subsequently in flasks with RPMI medium. Hybridomas were cloned by assaying supernatants of wells showing cellular growth for antibody titer using immunoblot technique and fluorescent antibody staining in cultures of human intestinal epithelial cell strain T84, and by limiting dilution from proper wells. The hybridoma cells were seeded at calculated concentration of 7 cells/well in microtiter plates, and screened by immunoblotting technique to verify and isolate clonal hybridoma cell strains. Antibodies were purified from culture supernatants of said hybridoma.

Example 3

Cell Staining

Human intestinal epithelial cells were fixed in 3% formalin in phosphate buffered saline (PBS) at room temperature for 15 minutes, and further treated with 0.2% Triton X-100 in PBS at room temperature for 15 minutes. After blocking the cells with 1% bovine serum albumin (BSA), the test substance was added and incubated for 30 minutes at room temperature. After subsequent washing, FITC-labeled anti-rat immunoglobulin antibody was added and incubated for 30 minutes at room temperature, followed by washing off unreacted antibody and examination with a fluorescent microscope.

Results of double immunofluorescent staining with monoclonal antibody to the TJ-related protein ZO-1 and the anti-human occludin monoclonal antibody of the present invention are shown in the figure. As totally the same staining pattern as that of ZO-1 (reported in the literature) was observed, the human protein of the present invention has proven to be a human homologue of the TJ adhesion molecule occludin.

Example 4

Expression of Occludin in Cerebrovascular Cells

Since cerebral vascular endothelial cells are thought to have a high electroresistant TJ, which form the brain-blood barrier unlike peripheral vascular endothelial cells, I examined the distribution and expression of occludin in cultured porcine brain vascular endothelial cells (PBEC) possessing the high electroresistant TJ and cultured porcine aortic endothelial cells (PAEC).

As porcine occludin cDNA fragment, a 363 base fragment was prepared by amplification with PCR technique using as primers 1359–1391 sense strand (Sequence No. 7) and 1692–1721 antisense strand (Sequence No. 8) from the human occludin DNA sequence (Sequence No. 1). The amino acid sequence based on analysis of the coding base sequence of said fragment showed a high degree of homology with amino acid sequences of human, mouse and canine occludins, thus verifying the fragment to be a cDNA for porcine occludin. $^{32}$P-labeled said fragment was used as a probe.

To prepare mRNA from the cultured cells, an agarose gel electrophoresed sample was transferred onto nitrocellulose membrane and hybridized with the c DNA probe under highly stringent conditions, using an RNA isolation kit (Stratagene). As a result, the occludin mRNA showed a strong band at about 2.4 kb in PBEC, whereas in PAEC, only a very weak band was noted at that position.

Expression of occludin in these cells was compared using anti-mouse occludin antibody as a monoclonal antibody specifically recognizing mammalian occludins and an antibody against the TJ-related protein ZO-1.

Anti-mouse occludin rat antibody was prepared using mouse occludin:glutathione-S-transferase fused protein as a antigen, and FITC-labeled anti-rat IgG sheep antibody was used for detection of said antibody. When equal protein quantities of extracts from disrupted cultured cells were analyzed by immunoblotting after one-dimensional gel electrophoresis, a strong band of occludin was detected at about 58 KD in PBEC while a considerably weaker band was noted at that position in PAEC. On the other hand, there was no appreciable difference in expression of ZO-1 between the two types of cells. With immunostaining, PBEC exhibited a marked occludin expression with the same continuous intercellular localization as ZO-1, as seen in the immunoblotting study. In PAEC, in contrast, occludin was scarcely detected and ZO-1 showed a discontinuous intercellular localization. These results suggest that the relatively marked expression of occludin in PBEC is required for the formation of the highly electroresistant TJ, and provide evidence that occludin is the constituent protein of the TJ.

What is claimed is:

1. A monoclonal antibody or a polyclonal antiserum comprising antibodies that specifically binds to at least one epitope of a mammalian occludin presented by an amino acid sequence of SEQ ID NOS:2, 4 or 6.

2. The monoclonal antibody of claim 1.

3. The polyclonal antiserum of claim 1 that specifically binds to at least one epitope presented by an amino acid sequence of SEQ ID NOS:2, 4 or 6.

4. A monoclonal antibody or polyclonal antiserum of claim 1 that specifically binds to at least one epitope of a human occludin presented by amino acids corresponding to amino acids 89–135 or 196–243 of SEQ ID NO: 2.

5. The monoclonal antibody of claim 4.

6. The monoclonal antibody or polyclonal antiserum of claim 4 that specifically binds to an epitope presented by amino acids 89–135 or 196–243 of SEQ ID NO:2.

7. A labeled antibody or labeled antiserum comprising the monoclonal antibody or polyclonal antiserum of any one of claims 1–3 or 4–6.

8. The labeled antibody or labeled antiserum of claim 7 that is labeled with a fluorescent agent, a radioactive substance, an enzyme, a metal or a dye.

9. The labeled antibody or labeled antiserum of claim 7 that is an Fab or Fab' fragment of said antibody.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
       (A) LENGTH: 2379 base pairs
       (B) TYPE: nucleic acid
       (C) STRANDEDNESS: double
       (D) TOPOLOGY: linear (ii) MOLECULE TYPE: cDNA (vi) ORIGINAL SOURCE:
       (A) ORGANISM: Homo sapiens
       (B) STRAIN: Cell strain T84
       (F) TISSUE TYPE: Epithelial, intestinal (ix) FEATURE:
       (A) NAME/KEY: CDS
       (B) LOCATION: 168..1733

(xi) SEQUENCE DESCRIPTION: SEQ ID NO:1:

```
CTCCCGCGTC CACCTCTCCC TCCCTGCTTC CTCTGGCGGA GGCGGCAGGA ACCGAGAGCC      60

AGGTCCAGAG CGCCGAGGAG CCGGTCTAGG ACGCAGCAGA TTGGTTTATC TTGGAAGCTA     120

AAGGGCATTG CTCATCCTGA AGATCAGCTG ACCATTGACA ATCAGCC ATG TCA TCC       176
                                                    Met Ser Ser
                                                     1

AGG CCT CTT GAA AGT CCA CCT CCT TAC AGG CCT GAT GAA TTC AAA CCG      224
Arg Pro Leu Glu Ser Pro Pro Pro Tyr Arg Pro Asp Glu Phe Lys Pro
  5              10                  15

AAT CAT TAT GCA CCA AGC AAT GAC ATA TAT GGT GGA GAG ATG CAT GTT      272
Asn His Tyr Ala Pro Ser Asn Asp Ile Tyr Gly Gly Glu Met His Val
 20                  25                  30                  35

CGA CCA ATG CTC TCT CAG CCA GCC TAC TCT TTT TAC CCA GAA GAT GAA      320
Arg Pro Met Leu Ser Gln Pro Ala Tyr Ser Phe Tyr Pro Glu Asp Glu
             40                  45                  50

ATT CTT CAC TTC TAC AAA TGG ACC TCT CCT CCA GGA GTG ATT CGG ATC      368
Ile Leu His Phe Tyr Lys Trp Thr Ser Pro Pro Gly Val Ile Arg Ile
         55                  60                  65

CTG TCT ATG CTC ATT ATT GTG ATG TGC ATT GCC ATC TTT GCC TGT GTG      416
Leu Ser Met Leu Ile Ile Val Met Cys Ile Ala Ile Phe Ala Cys Val
     70                  75                  80

GCC TCC ACG CTT GCC TGG GAC AGA GGC TAT GGA ACT TCC CTT TTA GGA      464
Ala Ser Thr Leu Ala Trp Asp Arg Gly Tyr Gly Thr Ser Leu Leu Gly
 85                  90                  95

GGT AGT GTA GGC TAC CCT TAT GGA GGA AGT GGC TTT GGT AGC TAC GGA      512
Gly Ser Val Gly Tyr Pro Tyr Gly Gly Ser Gly Phe Gly Ser Tyr Gly
100                 105                 110                 115

AGT GGC TAT GGC TAT GGC TAT GGT TAT GGC TAT GGC TAC GGA GGC TAT      560
Ser Gly Tyr Gly Tyr Gly Tyr Gly Tyr Gly Tyr Gly Tyr Gly Gly Tyr
                120                 125                 130

ACA GAC CCA AGA GCA GCA AAG GGC TTC ATG TTG GCC ATG GCT GCC TTT      608
Thr Asp Pro Arg Ala Ala Lys Gly Phe Met Leu Ala Met Ala Ala Phe
            135                 140                 145

TGT TTC ATT GCC GCG TTG GTG ATC TTT GTT ACC AGT GTT ATA AGA TCT      656
Cys Phe Ile Ala Ala Leu Val Ile Phe Val Thr Ser Val Ile Arg Ser
        150                 155                 160

GAA ATG TCC AGA ACA AGA AGA TAC TAC TTA AGT GTG ATA ATA GTG AGT      704
Glu Met Ser Arg Thr Arg Arg Tyr Tyr Leu Ser Val Ile Ile Val Ser
```

```
                165                     170                     175
GCT ATC CTG GGC ATC ATG GTG TTT ATT GCC ACA ATT GTC TAT ATA ATG      752
Ala Ile Leu Gly Ile Met Val Phe Ile Ala Thr Ile Val Tyr Ile Met
180                 185                     190                 195

GGA GTG AAC CCA ACT GCT CAG TCT TCT GGA TCT CTA TAT GGT TCA CAA      800
Gly Val Asn Pro Thr Ala Gln Ser Ser Gly Ser Leu Tyr Gly Ser Gln
                    200                     205                 210

ATA TAT GCC CTC TGC AAC CAA TTT TAT ACA CCT GCA GCT ACT GGA CTC      848
Ile Tyr Ala Leu Cys Asn Gln Phe Tyr Thr Pro Ala Ala Thr Gly Leu
                215                     220                 225

TAC GTG GAT CAG TAT TTG TAT CAC TAC TGT GTT GTG GAT CCC CAG GAG      896
Tyr Val Asp Gln Tyr Leu Tyr His Tyr Cys Val Val Asp Pro Gln Glu
            230                     235                 240

GCC ATT GCC ATT GTA CTG GGG TTC ATG ATT ATT GTG GCT TTT GCT TTA      944
Ala Ile Ala Ile Val Leu Gly Phe Met Ile Ile Val Ala Phe Ala Leu
245                     250                     255

ATA ATT TTC TTT GCT GTG AAA ACT CGA AGA AAG ATG GAC AGG TAT GAC      992
Ile Ile Phe Phe Ala Val Lys Thr Arg Arg Lys Met Asp Arg Tyr Asp
260                 265                     270                 275

AAG TCC AAT ATT TTG TGG GAC AAG GAA CAC ATT TAT GAT GAG CAG CCC     1040
Lys Ser Asn Ile Leu Trp Asp Lys Glu His Ile Tyr Asp Glu Gln Pro
                280                     285                 290

CCC AAT GTC GAG GAG TGG GTT AAA AAT GTG TCT GCA GGC ACA CAG GAC     1088
Pro Asn Val Glu Glu Trp Val Lys Asn Val Ser Ala Gly Thr Gln Asp
                295                     300                 305

GTG CCT TCA CCC CCA TCT GAC TAT GTG GAA AGA GTT GAC AGT CCC ATG     1136
Val Pro Ser Pro Pro Ser Asp Tyr Val Glu Arg Val Asp Ser Pro Met
            310                     315                 320

GCA TAC TCT TCC AAT GGC AAA GTG AAT GAC AAG CGG TTT TAT CCA GAG     1184
Ala Tyr Ser Ser Asn Gly Lys Val Asn Asp Lys Arg Phe Tyr Pro Glu
325                     330                     335

TCT TCC TAT AAA TCC ACG CCG GTT CCT GAA GTG GTT CAG GAG CTT CCA     1232
Ser Ser Tyr Lys Ser Thr Pro Val Pro Glu Val Val Gln Glu Leu Pro
340                 345                     350                 355

TTA ACT TCG CCT GTG GAT GAC TTC AGG CAG CCT CGT TAC AGC AGC GGT     1280
Leu Thr Ser Pro Val Asp Asp Phe Arg Gln Pro Arg Tyr Ser Ser Gly
                360                     365                 370

GGT AAC TTT GAG ACA CCT TCA AAA AGA GCA CCT GCA AAG GGA AGA GCA     1328
Gly Asn Phe Glu Thr Pro Ser Lys Arg Ala Pro Ala Lys Gly Arg Ala
                375                     380                 385

GGA AGG TCA AAG AGA ACA GAG CAA GAT CAC TAT GAG ACA GAC TAC ACA     1376
Gly Arg Ser Lys Arg Thr Glu Gln Asp His Tyr Glu Thr Asp Tyr Thr
            390                     395                 400

ACT GGC GGC GAG TCC TGT GAT GAG CTG GAG GAG GAC TGG ATC AGG GAA     1424
Thr Gly Gly Glu Ser Cys Asp Glu Leu Glu Glu Asp Trp Ile Arg Glu
405                     410                     415

TAT CCA CCT ATC ACT TCA GAT CAA CAA AGA CAA CTG TAC AAG AGG AAT     1472
Tyr Pro Pro Ile Thr Ser Asp Gln Gln Arg Gln Leu Tyr Lys Arg Asn
420                 425                     430                 435

TTT GAC ACT GGC TTA CAG GAA TAC AAG AGC TTA CAA TCA GAA CTT GAT     1520
Phe Asp Thr Gly Leu Gln Glu Tyr Lys Ser Leu Gln Ser Glu Leu Asp
                440                     445                 450

GAG ATC AAT AAA GAA CTC TCC CGT TTG GAT AAA GAA TTG GAT GAC TAT     1568
Glu Ile Asn Lys Glu Leu Ser Arg Leu Asp Lys Glu Leu Asp Asp Tyr
                455                     460                 465

AGA GAA GAA AGT GAA GAG TAC ATG GCT GCT GCT GAT GAA TAC AAT AGA     1616
Arg Glu Glu Ser Glu Glu Tyr Met Ala Ala Ala Asp Glu Tyr Asn Arg
            470                     475                 480

CTG AAG CAA GTG AAG GGA TCT GCA GAT TAC AAA AGT AAG AAG AAT CAT     1664
```

```
Leu Lys Gln Val Lys Gly Ser Ala Asp Tyr Lys Ser Lys Lys Asn His
    485                 490                 495

TGC AAG CAG TTA AAG AGC AAA TTG TCA CAC ATC AAG AAG ATG GTT GGA    1712
Cys Lys Gln Leu Lys Ser Lys Leu Ser His Ile Lys Lys Met Val Gly
500             505                 510                 515

GAC TAT GAT AGA CAG AAA ACA TAGAAGGCTG ATGCCAAGTT GTTTGAGAAA       1763
Asp Tyr Asp Arg Gln Lys Thr
                520

TTAAGTATCT GACATCTCTG CAATCTTCTC AGAAGGCAAA TGACTTTGGA CCATAACCCC  1823

GGAAGCCAAA CCTCTGTGAG CATCACAAAG TTTTGGTTGC TTTAACATCA TCAGTATTGA  1883

AGCATTTTAT AAATCGCTTT TGATAATCAA CTGGGCTGAA CACTCCAATT AAGGATTTTA  1943

TGCTTTAAAC ATTGGTTCTT GTATTAAGAA TGAAATACTG TTTGAGGTTT TTAAGCCTTA  2003

AAGGAAGGTT CTGGTGTGAA CTAAACTTTC ACACCCCAGA CGATGTCTTC ATACCTACAT  2063

GTATTTGTTT GCATAGGTGA TCTCATTTAA TCCTCTCAAC CACCTTTCAG ATAACTGTTA  2123

TTTATAATCA CTTTTTTCCA CATAAGGAAA CTGGGTTCCT GCAATGAAGT CTCTGAAGTG  2183

AAACTGCTTG TTTCCTAGCA CACACTTTTG GTTAAGTCTG TTTTATGACT TCATTAATAA  2243

TAAATTCCCT GGCCTTTCAT ATTTTAGCTA CTATATATGT GATGATCTAC CAGCCTCCCT  2303

ATTTTTTTTC TGTTATATAA ATGGTTAAAA GAGGTTTTTC TTAAATAATA AAGATCATGT  2363

AAAAGTAAAA AAAAAA                                                  2379

(2) INFORMATION FOR SEQ ID NO:2:

(i) SEQUENCE CHARACTERISTICS:
        (A) LENGTH: 522 amino acids
        (B) TYPE: amino acid
        (D) TOPOLOGY: linear (ii) MOLECULE TYPE: protein (xi) SEQUENCE DESCRIPTION: SEQ ID NO:2:

Met Ser Ser Arg Pro Leu Glu Ser Pro Pro Tyr Arg Pro Asp Glu
1               5                   10                  15

Phe Lys Pro Asn His Tyr Ala Pro Ser Asn Asp Ile Tyr Gly Gly Glu
                20                  25                  30

Met His Val Arg Pro Met Leu Ser Gln Pro Ala Tyr Ser Phe Tyr Pro
            35                  40                  45

Glu Asp Glu Ile Leu His Phe Tyr Lys Trp Thr Ser Pro Pro Gly Val
    50                  55                  60

Ile Arg Ile Leu Ser Met Leu Ile Val Met Cys Ile Ala Ile Phe
65                  70                  75                  80

Ala Cys Val Ala Ser Thr Leu Ala Trp Asp Arg Gly Tyr Gly Thr Ser
                85                  90                  95

Leu Leu Gly Gly Ser Val Gly Tyr Pro Tyr Gly Gly Ser Gly Phe Gly
                100                 105                 110

Ser Tyr Gly Ser Gly Tyr Gly Tyr Gly Tyr Gly Tyr Gly Tyr
            115                 120                 125

Gly Gly Tyr Thr Asp Pro Arg Ala Ala Lys Gly Phe Met Leu Ala Met
    130                 135                 140

Ala Ala Phe Cys Phe Ile Ala Ala Leu Val Ile Phe Val Thr Ser Val
145                 150                 155                 160

Ile Arg Ser Glu Met Ser Arg Thr Arg Arg Tyr Tyr Leu Ser Val Ile
                165                 170                 175

Ile Val Ser Ala Ile Leu Gly Ile Met Val Phe Ile Ala Thr Ile Val
```

```
                    180             185             190
Tyr Ile Met Gly Val Asn Pro Thr Ala Gln Ser Ser Gly Ser Leu Tyr
            195             200             205

Gly Ser Gln Ile Tyr Ala Leu Cys Asn Gln Phe Tyr Thr Pro Ala Ala
            210             215             220

Thr Gly Leu Tyr Val Asp Gln Tyr Leu Tyr His Tyr Cys Val Val Asp
225             230             235             240

Pro Gln Glu Ala Ile Ala Ile Val Leu Gly Phe Met Ile Val Ala
                245             250             255

Phe Ala Leu Ile Ile Phe Phe Ala Val Lys Thr Arg Arg Lys Met Asp
                260             265             270

Arg Tyr Asp Lys Ser Asn Ile Leu Trp Asp Lys Glu His Ile Tyr Asp
            275             280             285

Glu Gln Pro Pro Asn Val Glu Glu Trp Val Lys Asn Val Ser Ala Gly
            290             295             300

Thr Gln Asp Val Pro Ser Pro Pro Ser Asp Tyr Val Glu Arg Val Asp
305             310             315             320

Ser Pro Met Ala Tyr Ser Ser Asn Gly Lys Val Asn Asp Lys Arg Phe
                325             330             335

Tyr Pro Glu Ser Ser Tyr Lys Ser Thr Pro Val Pro Glu Val Val Gln
                340             345             350

Glu Leu Pro Leu Thr Ser Pro Val Asp Asp Phe Arg Gln Pro Arg Tyr
            355             360             365

Ser Ser Gly Gly Asn Phe Glu Thr Pro Ser Lys Arg Ala Pro Ala Lys
            370             375             380

Gly Arg Ala Gly Arg Ser Lys Arg Thr Glu Gln Asp His Tyr Glu Thr
385             390             395             400

Asp Tyr Thr Thr Gly Gly Glu Ser Cys Asp Glu Leu Glu Glu Asp Trp
                405             410             415

Ile Arg Glu Tyr Pro Pro Ile Thr Ser Asp Gln Gln Arg Gln Leu Tyr
                420             425             430

Lys Arg Asn Phe Asp Thr Gly Leu Gln Glu Tyr Lys Ser Leu Gln Ser
            435             440             445

Glu Leu Asp Glu Ile Asn Lys Glu Leu Ser Arg Leu Asp Lys Glu Leu
450             455             460

Asp Asp Tyr Arg Glu Glu Ser Glu Glu Tyr Met Ala Ala Ala Asp Glu
465             470             475             480

Tyr Asn Arg Leu Lys Gln Val Lys Gly Ser Ala Asp Tyr Lys Ser Lys
                485             490             495

Lys Asn His Cys Lys Gln Leu Lys Ser Lys Leu Ser His Ile Lys Lys
                500             505             510

Met Val Gly Asp Tyr Asp Arg Gln Lys Thr
                515             520

(2) INFORMATION FOR SEQ ID NO:3:

(i) SEQUENCE CHARACTERISTICS:
        (A) LENGTH: 1961 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Canine
        (B) STRAIN: MDCK
```

(F) TISSUE TYPE: Kidney cell (ix) FEATURE:
    (A) NAME/KEY: CDS
    (B) LOCATION: 72..1634

(xi) SEQUENCE DESCRIPTION: SEQ ID NO:3:

```
CAGGTTGGCT TATTTTGGGG AGCTCTGGGA TCCTGCTCGT CCTGAAGATC GGGTGATCAT        60

TGACATCAGC C ATG TCA TCG AGG CCT TTT GAG AGT CCA CCT CCG TAT AGA       110
             Met Ser Ser Arg Pro Phe Glu Ser Pro Pro Pro Tyr Arg
                  1               5                  10

CCT GAT GAA TTC AAA CCC AAT CAT TAT GCA CCG AGC AAT GAT GTG TAC        158
Pro Asp Glu Phe Lys Pro Asn His Tyr Ala Pro Ser Asn Asp Val Tyr
         15                  20                  25

GGT GGG GAC ATG CAC GTC CGA CCC ATG CTC TCT CAG CCG GCG TAT TCT        206
Gly Gly Asp Met His Val Arg Pro Met Leu Ser Gln Pro Ala Tyr Ser
 30                  35                  40                  45

TTC TAC CCA GAA GAT GAA ATT CTT CAC TTC TAC AAA TGG ACC TCT CCT        254
Phe Tyr Pro Glu Asp Glu Ile Leu His Phe Tyr Lys Trp Thr Ser Pro
                 50                  55                  60

CCA GGA GTA ATT CGG ATT CTG TCC ATG CTT GTC ATT GTG ATG TGC ATC        302
Pro Gly Val Ile Arg Ile Leu Ser Met Leu Val Ile Val Met Cys Ile
             65                  70                  75

GCC ATA TTT GGC TGT GTC GCG TCC ACG CTC GCC TGG GAT AGA GGC TAT        350
Ala Ile Phe Gly Cys Val Ala Ser Thr Leu Ala Trp Asp Arg Gly Tyr
         80                  85                  90

GGA ACT GGC TTA ATG GGT GGT AGC ATA GGC TAC CCT TAC GGA AGT GGC        398
Gly Thr Gly Leu Met Gly Gly Ser Ile Gly Tyr Pro Tyr Gly Ser Gly
     95                  100                 105

TTC GGG AGC TAC GGG ACT GGC TAC GGC TAC GGG TTT GGC TAC GGC TAC        446
Phe Gly Ser Tyr Gly Thr Gly Tyr Gly Tyr Gly Phe Gly Tyr Gly Tyr
110                 115                 120                 125

GGC TAC GGC GGC TAC ACG GAT CCC AGA GCA GCA AAG GGC TTC CTC CTG        494
Gly Tyr Gly Gly Tyr Thr Asp Pro Arg Ala Ala Lys Gly Phe Leu Leu
                 130                 135                 140

GCC ATG GTG GCC TTT TGT TTT ATC GCT GCA TTG GTG ATA TTT GTT ACC        542
Ala Met Val Ala Phe Cys Phe Ile Ala Ala Leu Val Ile Phe Val Thr
             145                 150                 155

AGC GTT ATA AGG TCT GAC ATA TCC AGA ACC AGA AGG TAC TAC TTG ACT        590
Ser Val Ile Arg Ser Asp Ile Ser Arg Thr Arg Arg Tyr Tyr Leu Thr
         160                 165                 170

GTA ATA ATA CTG AGT GCC TTC CTG GGC GTC ATG ATG TTC ATT GCT ACA        638
Val Ile Ile Leu Ser Ala Phe Leu Gly Val Met Met Phe Ile Ala Thr
     175                 180                 185

ATT GTC TAT ATA ATG GGA GTC AAT CCA ACT GCC CAG GCT TCT GGG TCT        686
Ile Val Tyr Ile Met Gly Val Asn Pro Thr Ala Gln Ala Ser Gly Ser
190                 195                 200                 205

TTA TAC AGT TCA CAG ATA TAT GCC ATG TGC AAC CAG TTC TAT GCA TCT        734
Leu Tyr Ser Ser Gln Ile Tyr Ala Met Cys Asn Gln Phe Tyr Ala Ser
                 210                 215                 220

ACA GCT ACC GGA CTC TAC ATG GAT CAG TAT TTG TAT CAC TAC TGT GTG        782
Thr Ala Thr Gly Leu Tyr Met Asp Gln Tyr Leu Tyr His Tyr Cys Val
             225                 230                 235

GTG GAT CCC CAA GAG GCA ATT GCC ATT GTC CTG GGA TTC ATG GTG ATT        830
Val Asp Pro Gln Glu Ala Ile Ala Ile Val Leu Gly Phe Met Val Ile
         240                 245                 250

GTG GCT TTT GCT TTA ATA ATT TTC TTT GCT GTG AAA ACT CGA AGA AAG        878
Val Ala Phe Ala Leu Ile Ile Phe Phe Ala Val Lys Thr Arg Arg Lys
     255                 260                 265

ATG GAC CGG TAT GAC AAG TCG AAT ATA TTG TGG GAC AAG GAA CAT ATT        926
```

```
Met Asp Arg Tyr Asp Lys Ser Asn Ile Leu Trp Asp Lys Glu His Ile
270                 275                 280                 285

TAT GAT GAA CAA CCC CCC AAT GTT GAA GAG TGG GTT AAA AAC GTT TCT      974
Tyr Asp Glu Gln Pro Pro Asn Val Glu Glu Trp Val Lys Asn Val Ser
                290                 295                 300

GCA GGC ACA CAA GAC ATG CCT CCT CCC CCT TCT GAC TAT GTG GAG AGA     1022
Ala Gly Thr Gln Asp Met Pro Pro Pro Pro Ser Asp Tyr Val Glu Arg
            305                 310                 315

GTG GAC AGT CCC ATG GCG TAC TCT TCC AAT GGT AAA GTG AAT GAC AAG     1070
Val Asp Ser Pro Met Ala Tyr Ser Ser Asn Gly Lys Val Asn Asp Lys
        320                 325                 330

CGG TTG TAT CCA GAG TCT TCC TAT AAA TCA ACA CCG GTC CCC GAA GTG     1118
Arg Leu Tyr Pro Glu Ser Ser Tyr Lys Ser Thr Pro Val Pro Glu Val
    335                 340                 345

GTG CAG GAG CTG CCC GCC ACC TCC CCT GCG GAT GAC TTC AGG CAG CCT     1166
Val Gln Glu Leu Pro Ala Thr Ser Pro Ala Asp Asp Phe Arg Gln Pro
350                 355                 360                 365

CGC TAC AGC AGC AGC GGG CAC TTG GAG CCA CCT TCG AAG AGG GCC CCC     1214
Arg Tyr Ser Ser Ser Gly His Leu Glu Pro Pro Ser Lys Arg Ala Pro
                370                 375                 380

TCG AAA GGA AGA ACG GGA AGG CCC AAG AGG CTG GAG CAG GAC CAC TAT     1262
Ser Lys Gly Arg Thr Gly Arg Pro Lys Arg Leu Glu Gln Asp His Tyr
            385                 390                 395

GAG ACA GAC TAC ACG ACG GGC GGC GAG TCG TGT GAC GAG CTG GAG GAG     1310
Glu Thr Asp Tyr Thr Thr Gly Gly Glu Ser Cys Asp Glu Leu Glu Glu
        400                 405                 410

GAC TGG ATC AGG GAA TAT CCA CCT ATC ACT TCA GAT CAA CAA AGA CAA     1358
Asp Trp Ile Arg Glu Tyr Pro Pro Ile Thr Ser Asp Gln Gln Arg Gln
    415                 420                 425

CTC TAC AAG AGA AAT TTT GAC ACT GGC CTG CAG GAA TAC AAG AGC TTA     1406
Leu Tyr Lys Arg Asn Phe Asp Thr Gly Leu Gln Glu Tyr Lys Ser Leu
430                 435                 440                 445

CAA GCA GAA CTT GAT GAG ATC AAT AAA GAA CTC TCT CGC CTG GAT AAA     1454
Gln Ala Glu Leu Asp Glu Ile Asn Lys Glu Leu Ser Arg Leu Asp Lys
                450                 455                 460

GAA TTG GAT GAC TAT AGA GAA GAA AGT GAA GAG TAC ATG GCT GCT GCT     1502
Glu Leu Asp Asp Tyr Arg Glu Glu Ser Glu Glu Tyr Met Ala Ala Ala
            465                 470                 475

GAT GAG TAC AAT AGA CTG AAG CAA GTT AAG GGA TCT CCA GAT TAC AAA     1550
Asp Glu Tyr Asn Arg Leu Lys Gln Val Lys Gly Ser Pro Asp Tyr Lys
        480                 485                 490

AAT AAG AGG AAT TAT TGC AAG CAG TTG AAG AGC AAA TTG TCC CAC ATC     1598
Asn Lys Arg Asn Tyr Cys Lys Gln Leu Lys Ser Lys Leu Ser His Ile
    495                 500                 505

AAG AAG ATG GTT GGA GAC TAT GAT AGA CAG AAA ACA TAGAAGGCAG          1644
Lys Lys Met Val Gly Asp Tyr Asp Arg Gln Lys Thr
510                 515                 520

ATGCCACACA GTTGAGAGA TTGTGAAGTA TTTGACATAT CTGCAACGTT GTCAGAAGGC    1704

AGAATGACTT TGGATTTCGA ACCCAGGAGG CCAGATCTTT GTGATCATTA CAAAGTTTTG   1764

GTAGCTTTAA TATCATCAGT ATTGAAGCAT TTTACACATA GCTTTTGATA ATCAACTGGG   1824

CTGAACACTC CCGATTAAGG ATTCTGTGCT TTAGACTTTG GCTGTTGTGC TAAAGGACTG   1884

AGTATAGGTG GAGGTTTTCA GACCTTGGAA GAAGGTCCCA CGGTGAACTT GTGCTGTGAA   1944

CTTGCACACT TGGGGCA                                                 1961
```

(2) INFORMATION FOR SEQ ID NO:4:

(i) SEQUENCE CHARACTERISTICS:

(A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO:4:

Met Ser Ser Arg Pro Phe Glu Ser Pro Pro Tyr Arg Pro Asp Glu
 1               5                  10                  15

Phe Lys Pro Asn His Tyr Ala Pro Ser Asn Asp Val Tyr Gly Gly Asp
                20                  25                  30

Met His Val Arg Pro Met Leu Ser Gln Pro Ala Tyr Ser Phe Tyr Pro
                35                  40                  45

Glu Asp Glu Ile Leu His Phe Tyr Lys Trp Thr Ser Pro Pro Gly Val
        50                  55                  60

Ile Arg Ile Leu Ser Met Leu Val Ile Val Met Cys Ile Ala Ile Phe
65                  70                  75                  80

Gly Cys Val Ala Ser Thr Leu Ala Trp Asp Arg Gly Tyr Gly Thr Gly
                85                  90                  95

Leu Met Gly Gly Ser Ile Gly Tyr Pro Tyr Gly Ser Gly Phe Gly Ser
                100                 105                 110

Tyr Gly Thr Gly Tyr Gly Tyr Gly Phe Gly Tyr Gly Tyr Gly Tyr Gly
                115                 120                 125

Gly Tyr Thr Asp Pro Arg Ala Ala Lys Gly Phe Leu Leu Ala Met Val
        130                 135                 140

Ala Phe Cys Phe Ile Ala Ala Leu Val Ile Phe Val Thr Ser Val Ile
145                 150                 155                 160

Arg Ser Asp Ile Ser Arg Thr Arg Arg Tyr Tyr Leu Thr Val Ile Ile
                165                 170                 175

Leu Ser Ala Phe Leu Gly Val Met Met Phe Ile Ala Thr Ile Val Tyr
                180                 185                 190

Ile Met Gly Val Asn Pro Thr Ala Gln Ala Ser Gly Ser Leu Tyr Ser
                195                 200                 205

Ser Gln Ile Tyr Ala Met Cys Asn Gln Phe Tyr Ala Ser Thr Ala Thr
        210                 215                 220

Gly Leu Tyr Met Asp Gln Tyr Leu Tyr His Tyr Cys Val Val Asp Pro
225                 230                 235                 240

Gln Glu Ala Ile Ala Ile Val Leu Gly Phe Met Val Ile Val Ala Phe
                245                 250                 255

Ala Leu Ile Ile Phe Phe Ala Val Lys Thr Arg Arg Lys Met Asp Arg
                260                 265                 270

Tyr Asp Lys Ser Asn Ile Leu Trp Asp Lys Glu His Ile Tyr Asp Glu
        275                 280                 285

Gln Pro Pro Asn Val Glu Glu Trp Val Lys Asn Val Ser Ala Gly Thr
290                 295                 300

Gln Asp Met Pro Pro Pro Ser Asp Tyr Val Glu Arg Val Asp Ser
305                 310                 315                 320

Pro Met Ala Tyr Ser Ser Asn Gly Lys Val Asn Asp Lys Arg Leu Tyr
                325                 330                 335

Pro Glu Ser Ser Tyr Lys Ser Thr Pro Val Pro Glu Val Val Gln Glu
        340                 345                 350

Leu Pro Ala Thr Ser Pro Ala Asp Asp Phe Arg Gln Pro Arg Tyr Ser
                355                 360                 365

Ser Ser Gly His Leu Glu Pro Pro Ser Lys Arg Ala Pro Ser Lys Gly
        370                 375                 380

```
Arg Thr Gly Arg Pro Lys Arg Leu Glu Gln Asp His Tyr Glu Thr Asp
385                 390                 395                 400

Tyr Thr Thr Gly Gly Glu Ser Cys Asp Glu Leu Glu Glu Asp Trp Ile
            405                 410                 415

Arg Glu Tyr Pro Pro Ile Thr Ser Asp Gln Gln Arg Gln Leu Tyr Lys
            420                 425                 430

Arg Asn Phe Asp Thr Gly Leu Gln Glu Tyr Lys Ser Leu Gln Ala Glu
            435                 440                 445

Leu Asp Glu Ile Asn Lys Glu Leu Ser Arg Leu Asp Lys Glu Leu Asp
    450                 455                 460

Asp Tyr Arg Glu Glu Ser Glu Glu Tyr Met Ala Ala Asp Glu Tyr
465                 470                 475                 480

Asn Arg Leu Lys Gln Val Lys Gly Ser Pro Asp Tyr Lys Asn Lys Arg
                485                 490                 495

Asn Tyr Cys Lys Gln Leu Lys Ser Lys Leu Ser His Ile Lys Lys Met
                500                 505                 510

Val Gly Asp Tyr Asp Arg Gln Lys Thr
            515                 520
```

(2) INFORMATION FOR SEQ ID NO:5:

(i) SEQUENCE CHARACTERISTICS:
        (A) LENGTH: 2839 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Mouse
        (F) TISSUE TYPE: Lung cell (ix) FEATURE:
        (A) NAME/KEY: CDS
        (B) LOCATION: 223..1785

(xi) SEQUENCE DESCRIPTION: SEQ ID NO:5:

```
GGAGTTTCAG GTGAATGGGT CACCGAGGGA GGAGGCTGGC CACGCCACAC CTCGTCGCTA      60

GTGCCCACCT CCCGGCCCCT CTTTCCTTAG GCGACAGCGG TGGAGTTGCG GGAGAGCGGT     120

CCAGCGCACG GAGCAACCGG CTAGGGGCTC GGCAGGTTCG CTTATCTTGG GAGCCTGGAC     180

ATTTTGCTCA TCATAAAGAT TAGGTGACCA GTGACATCAG CC ATG TCC GTG AGG        234
                                              Met Ser Val Arg
                                                1

CCT TTT GAA AGT CCA CCT CCT TAC AGA CCT GAT GAA TTC AAA CCC AAT      282
Pro Phe Glu Ser Pro Pro Pro Tyr Arg Pro Asp Glu Phe Lys Pro Asn
  5                  10                  15                  20

CAT TAT GCA CCA AGC AAT GAC ATG TAT GGC GGA GAG ATG CAT GTC CGG      330
His Tyr Ala Pro Ser Asn Asp Met Tyr Gly Gly Glu Met His Val Arg
              25                  30                  35

CCG ATG CTC TCT CAG CCA GCG TAC TCT TTT TAT CCG GAA GAT GAA ATT      378
Pro Met Leu Ser Gln Pro Ala Tyr Ser Phe Tyr Pro Glu Asp Glu Ile
              40                  45                  50

CTT CAC TTC TAC AAA TGG ACG TCG CCC CCA GGG GTG ATC CGG ATC CTG      426
Leu His Phe Tyr Lys Trp Thr Ser Pro Pro Gly Val Ile Arg Ile Leu
      55                  60                  65

TCT ATG CTC ATT ATT GTG ATG TGC ATC GCC ATA TTT GCC TGT GTG GCT      474
Ser Met Leu Ile Ile Val Met Cys Ile Ala Ile Phe Ala Cys Val Ala
  70                  75                  80
```

```
TCC ACA CTT GCT TGG GAC AGA GGC TAT GGG ACA GGG CTC TTT GGA GGA          522
Ser Thr Leu Ala Trp Asp Arg Gly Tyr Gly Thr Gly Leu Phe Gly Gly
 85                  90                  95                 100

AGC CTA AAC TAC CCT TAT AGT GGC TTT GGC TAC GGA GGT GGC TAT GGA          570
Ser Leu Asn Tyr Pro Tyr Ser Gly Phe Gly Tyr Gly Gly Gly Tyr Gly
                105                 110                 115

GGC GGC TAT GGA GGC TAT GGC TAT GGC TAT GGA TAT ACA GAC CCA              618
Gly Gly Tyr Gly Gly Tyr Gly Tyr Gly Tyr Gly Tyr Thr Asp Pro
        120                 125                 130

AGA GCA GCC AAA GGC TTC CTG TTG GCC ATG GCA GCC TTC TGC TTC ATC          666
Arg Ala Ala Lys Gly Phe Leu Leu Ala Met Ala Ala Phe Cys Phe Ile
            135                 140                 145

GCT TCC TTA GTA ATA TTT GTG ACC AGT GTT ATA AGA TCT GGA ATG TCC          714
Ala Ser Leu Val Ile Phe Val Thr Ser Val Ile Arg Ser Gly Met Ser
150                 155                 160

AGG ACA AGA AGA TAT TAC TTG ATC GTG ATC ATA GTC AGC GCT ATC CTG          762
Arg Thr Arg Arg Tyr Tyr Leu Ile Val Ile Ile Val Ser Ala Ile Leu
165                 170                 175                 180

GGC ATC ATG GTG TTT ATT GCC ACG ATC GTG TAC ATA ATG GGA GTG AAC          810
Gly Ile Met Val Phe Ile Ala Thr Ile Val Tyr Ile Met Gly Val Asn
                185                 190                 195

CCG ACG GCC CAG GCT TCT GGA TCT ATG TAC GGC TCA CAG ATA TAT ATG          858
Pro Thr Ala Gln Ala Ser Gly Ser Met Tyr Gly Ser Gln Ile Tyr Met
            200                 205                 210

ATC TGC AAC CAG TTT TAT ACT CCT GGA GGT ACT GGT CTC TAC GTG GAT          906
Ile Cys Asn Gln Phe Tyr Thr Pro Gly Gly Thr Gly Leu Tyr Val Asp
            215                 220                 225

CAA TAT TTG TAT CAC TAC TGT GTG GTT GAT CCC CAG GAG GCT ATA GCC          954
Gln Tyr Leu Tyr His Tyr Cys Val Val Asp Pro Gln Glu Ala Ile Ala
        230                 235                 240

ATT GTC CTG GGG TTC ATG ATT ATC GTG GCT TTT GCT TTA ATC ATC TTT         1002
Ile Val Leu Gly Phe Met Ile Ile Val Ala Phe Ala Leu Ile Ile Phe
245                 250                 255                 260

TTT GCT GTG AAA ACC CGA AGA AAG ATG GAT CGG TAT GAT AAG TCC AAT         1050
Phe Ala Val Lys Thr Arg Arg Lys Met Asp Arg Tyr Asp Lys Ser Asn
                265                 270                 275

ATT TTG TGG GAT AAG GAA CAC ATT TAT GAT GAA CAG CCC CCC AAT GTT         1098
Ile Leu Trp Asp Lys Glu His Ile Tyr Asp Glu Gln Pro Pro Asn Val
            280                 285                 290

GAA GAG TGG GTT AAA AAT GTG TCT GCA GGC ACA CAG GAC ATG CCT CCA         1146
Glu Glu Trp Val Lys Asn Val Ser Ala Gly Thr Gln Asp Met Pro Pro
            295                 300                 305

CCC CCA TCT GAC TAT GCG GAA AGA GTT GAC AGT CCA ATG GCC TAC TCC         1194
Pro Pro Ser Asp Tyr Ala Glu Arg Val Asp Ser Pro Met Ala Tyr Ser
        310                 315                 320

TCC AAT GGC AAA GTG AAT GGC AAG CGA TCA TAC CCA GAG TCT TTC TAT         1242
Ser Asn Gly Lys Val Asn Gly Lys Arg Ser Tyr Pro Glu Ser Phe Tyr
325                 330                 335                 340

AAG TCA ACA CCT CTG GTG CCT GAA GTG GCC CAG GAG ATT CCT CTG ACC         1290
Lys Ser Thr Pro Leu Val Pro Glu Val Ala Gln Glu Ile Pro Leu Thr
                345                 350                 355

TTG AGT GTG GAT GAC TTC AGG CAG CCT CGG TAC AGC AGC AAT GGT AAC         1338
Leu Ser Val Asp Asp Phe Arg Gln Pro Arg Tyr Ser Ser Asn Gly Asn
            360                 365                 370

CTA GAG ACA CCT TCT AAA AGG GCT CCC ACG AAG GGG AAA GCA GGA AAG         1386
Leu Glu Thr Pro Ser Lys Arg Ala Pro Thr Lys Gly Lys Ala Gly Lys
            375                 380                 385

GGC AAG AGG ACG GAC CCT GAC CAC TAT GAA ACA GAC TAC ACG ACA GGT         1434
Gly Lys Arg Thr Asp Pro Asp His Tyr Glu Thr Asp Tyr Thr Thr Gly
390                 395                 400
```

```
GGG GAG TCC TGC GAG GAG CTG GAG GAG GAC TGG GTC AGG GAA TAT CCA     1482
Gly Glu Ser Cys Glu Glu Leu Glu Glu Asp Trp Val Arg Glu Tyr Pro
405                 410                 415                 420

CCT ATC ACT TCA GAT CAA CAA AGA CAA CTC TAC AAG AGA AAT TTT GAT     1530
Pro Ile Thr Ser Asp Gln Gln Arg Gln Leu Tyr Lys Arg Asn Phe Asp
                425                 430                 435

GCA GGT CTG CAG GAG TAT AAG AGC TTA CAG GCA GAA CTA GAC GAC GTC     1578
Ala Gly Leu Gln Glu Tyr Lys Ser Leu Gln Ala Glu Leu Asp Asp Val
            440                 445                 450

AAT AAA GAG CTC TCT CGT CTA GAT AAA GAG CTG GAT GAC TAC AGA GAG     1626
Asn Lys Glu Leu Ser Arg Leu Asp Lys Glu Leu Asp Asp Tyr Arg Glu
        455                 460                 465

GAG AGT GAA GAG TAC ATG GCT GCT GCT GAT GAA TAT AAT AGA CTA AAG     1674
Glu Ser Glu Glu Tyr Met Ala Ala Ala Asp Glu Tyr Asn Arg Leu Lys
    470                 475                 480

CAA GTT AAG GGA TCT GCA GAT TAT AAA AGT AAG AGG AAT TAC TGC AAG     1722
Gln Val Lys Gly Ser Ala Asp Tyr Lys Ser Lys Arg Asn Tyr Cys Lys
485                 490                 495                 500

CAG TTG AAG AGC AAA TTA TCG CAC ATC AAG AGG ATG GTG GGA GAC TAT     1770
Gln Leu Lys Ser Lys Leu Ser His Ile Lys Arg Met Val Gly Asp Tyr
                505                 510                 515

GAC AGA CGG AAA CCT TAGAGAGATG CCAGTTGCGG GAGAAGGGAG AGGTGCATCT     1825
Asp Arg Arg Lys Pro
            520

GCCTGCACGA TGTCTCTGCA ATTCTCTCCA GAGGCAAACT GACTTTGGAC TCTAATCTGG   1885

GAAGTTAAAA CTTTGTGATC ATTACAAAGT TTCCATGGCT TTAATTCCAT CAGTTTCCTA   1945

TCTCCAGTAT TGAAGCATTT TATAAATGGC TTTTGATAAT TGACTGGGCT GAACACTCCA   2005

ATTAAGGATT TTACAGTTTC AACATTGATT CTTGTATTAA GAATTAAAAT GTTGCTTGAG   2065

GTTTTAAATG TCAAGAAAGG TCCTGGTGTG AGCTGTGATG TGTGTGAGCT GTGATGTGAA   2125

GGTTCACACG CCAGGCAGCG TGTTCCTCCA GGTAGACCGT CTAATCAATC TTTGCAGCAG   2185

CCCTCAGGTG ACTGTTATTT AGAATCAGGT TGTTTTTGGT TTTCCAGACA GGGTTTCTCT   2245

GTGTAGCCCT GGCTGACCTA GAACTTACGC TGTAGACCAG GCTGGCCTTG AACTCACACA   2305

GCTCCTCTGA GTGCTGGTGC AGGAGTTAAC GTCGTGGACC GGTATCATCA CTTTTCCTGC   2365

GGTGACTTCT CCAAACTGAA ACTGCTAAGG CAGTTTTGGC TAAGTCTGTT TTATGACTGC   2425

AAATGACAGC ATTCCTGCCT TTGTATTTCA GGGGAAATAC GATACATTAT ATCGGCCATG   2485

TTCCCCACCA CTGTTTTTCT TATATTGACT TTTAACAAAT GAATAGGATT ATTTTTGGCT   2545

TTACATTTTT TCCTAACACT TAAGATCATA TAAAATTAAC AAATATGTGA AATTTAAGAA   2605

TTGTAAATAT ATATTTACGT TTGAAAGATG ATTTTAAATC CAGGGTTAAA GTGCTTTTTA   2665

TCTTGTATAG TTTACATGCT TTTTTTTTTT TTTGATAACC CACTAGACCT TTCCATTGTA   2725

TCAGAGTATC CAATTACATT TACAATTATG ACTTGAATTG TATTTCACAG GAATGCTCAA   2785

GTTTTGTACA TATTTTATAA GGTATTAAAC CTGATGTTCT CTTTCTAAAA AAAA          2839
```

(2) INFORMATION FOR SEQ ID NO:6:

(i) SEQUENCE CHARACTERISTICS:
        (A) LENGTH: 521 amino acids
        (B) TYPE: amino acid
        (D) TOPOLOGY: linear (ii) MOLECULE TYPE: protein (xi) SEQUENCE DESCRIPTION: SEQ ID NO:6:

-continued

```
Met Ser Val Arg Pro Phe Glu Ser Pro Pro Tyr Arg Pro Asp Glu
 1               5                  10                  15

Phe Lys Pro Asn His Tyr Ala Pro Ser Asn Asp Met Tyr Gly Gly Glu
                20                  25                  30

Met His Val Arg Pro Met Leu Ser Gln Pro Ala Tyr Ser Phe Tyr Pro
            35                  40                  45

Glu Asp Glu Ile Leu His Phe Tyr Lys Trp Thr Ser Pro Pro Gly Val
    50                  55                  60

Ile Arg Ile Leu Ser Met Leu Ile Ile Val Met Cys Ile Ala Ile Phe
65                  70                  75                  80

Ala Cys Val Ala Ser Thr Leu Ala Trp Asp Arg Gly Tyr Gly Thr Gly
                85                  90                  95

Leu Phe Gly Gly Ser Leu Asn Tyr Pro Tyr Ser Gly Phe Gly Tyr Gly
            100                 105                 110

Gly Gly Tyr Gly Gly Gly Tyr Gly Gly Tyr Gly Tyr Gly Tyr Gly Gly
        115                 120                 125

Tyr Thr Asp Pro Arg Ala Ala Lys Gly Phe Leu Leu Ala Met Ala Ala
    130                 135                 140

Phe Cys Phe Ile Ala Ser Leu Val Ile Phe Val Thr Ser Val Ile Arg
145                 150                 155                 160

Ser Gly Met Ser Arg Thr Arg Arg Tyr Tyr Leu Ile Val Ile Ile Val
                165                 170                 175

Ser Ala Ile Leu Gly Ile Met Val Phe Ile Ala Thr Ile Val Tyr Ile
            180                 185                 190

Met Gly Val Asn Pro Thr Ala Gln Ala Ser Gly Ser Met Tyr Gly Ser
        195                 200                 205

Gln Ile Tyr Met Ile Cys Asn Gln Phe Tyr Thr Pro Gly Gly Thr Gly
    210                 215                 220

Leu Tyr Val Asp Gln Tyr Leu Tyr His Tyr Cys Val Val Asp Pro Gln
225                 230                 235                 240

Glu Ala Ile Ala Ile Val Leu Gly Phe Met Ile Ile Val Ala Phe Ala
                245                 250                 255

Leu Ile Ile Phe Phe Ala Val Lys Thr Arg Arg Lys Met Asp Arg Tyr
            260                 265                 270

Asp Lys Ser Asn Ile Leu Trp Asp Lys Glu His Ile Tyr Asp Glu Gln
        275                 280                 285

Pro Pro Asn Val Glu Glu Trp Val Lys Asn Val Ser Ala Gly Thr Gln
    290                 295                 300

Asp Met Pro Pro Pro Ser Asp Tyr Ala Glu Arg Val Asp Ser Pro
305                 310                 315                 320

Met Ala Tyr Ser Ser Asn Gly Lys Val Asn Gly Lys Arg Ser Tyr Pro
                325                 330                 335

Glu Ser Phe Tyr Lys Ser Thr Pro Leu Val Pro Glu Val Ala Gln Glu
            340                 345                 350

Ile Pro Leu Thr Leu Ser Val Asp Asp Phe Arg Gln Pro Arg Tyr Ser
        355                 360                 365

Ser Asn Gly Asn Leu Glu Thr Pro Ser Lys Arg Ala Pro Thr Lys Gly
    370                 375                 380

Lys Ala Gly Lys Gly Lys Arg Thr Asp Pro Asp His Tyr Glu Thr Asp
385                 390                 395                 400

Tyr Thr Thr Gly Gly Glu Ser Cys Glu Glu Leu Glu Glu Asp Trp Val
                405                 410                 415

Arg Glu Tyr Pro Pro Ile Thr Ser Asp Gln Gln Arg Gln Leu Tyr Lys
```

-continued

```
                    420                 425                 430
Arg Asn Phe Asp Ala Gly Leu Gln Glu Tyr Lys Ser Leu Gln Ala Glu
        435                 440                 445

Leu Asp Asp Val Asn Lys Glu Leu Ser Arg Leu Asp Lys Glu Leu Asp
    450                 455                 460

Asp Tyr Arg Glu Glu Ser Glu Glu Tyr Met Ala Ala Ala Asp Glu Tyr
465                 470                 475                 480

Asn Arg Leu Lys Gln Val Lys Gly Ser Ala Asp Tyr Lys Ser Lys Arg
            485                 490                 495

Asn Tyr Cys Lys Gln Leu Lys Ser Lys Leu Ser His Ile Lys Arg Met
            500                 505                 510

Val Gly Asp Tyr Asp Arg Arg Lys Pro
515 520
```

(2) INFORMATION FOR SEQ ID NO:7:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthesis DNA"

(xi) SEQUENCE DESCRIPTION: SEQ ID NO:7:

TATGAGACAG ACTACACAAC TGGCGGCGAG TCC                    33

(2) INFORMATION FOR SEQ ID NO:8:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Synthesis DNA"

(xi) SEQUENCE DESCRIPTION: SEQ ID NO:8:

ATCATAGTCT CCAACCATCT TCTTGATGTG                       30